United States Patent [19]

Christopfel et al.

[11] 4,376,870

[45] Mar. 15, 1983

[54] OPTICALLY ACTIVE PHOSPHINE COMPOUNDS

[75] Inventors: William C. Christopfel, Oakland, Calif.; William S. Knowles, St. Louis, Mo.

[73] Assignee: Monsanto Company, St. Louis, Mo.

[21] Appl. No.: 213,272

[22] Filed: Dec. 5, 1980

[51] Int. Cl.³ .......................... C07F 9/50; C07F 9/53
[52] U.S. Cl. .................................. 568/15; 568/13; 568/14; 260/429 R
[58] Field of Search .............................. 568/14, 13, 15

[56] References Cited

U.S. PATENT DOCUMENTS

| | | | |
|---|---|---|---|
| 3,849,480 | 11/1974 | Knowles et al. | 260/429 R X |
| 3,949,000 | 4/1976 | Violet | 260/429 R X |
| 4,008,281 | 2/1977 | Knowles et al. | 260/429 R X |
| 4,119,652 | 10/1978 | Knowles et al. | 260/429 R |
| 4,166,824 | 9/1979 | Henderson | 568/17 |
| 4,201,714 | 5/1980 | Hughes | 260/429 R X |
| 4,294,989 | 10/1981 | Knowles et al. | 260/429 R X |

OTHER PUBLICATIONS

Frysuk, Jour. Amer. Chem. Soc. vol. 100, 1978, pp. 5491-5494.
King, Jour. Org. Chem. 44, No. 10, pp. 1729-1731 (1979).

Primary Examiner—Helen M. S. Sneed

[57] ABSTRACT

The invention is a new family of phosphine compounds which can be used to make optically active metal coordination complex catalysts which combine high efficiency with a capability of performing rapidly (high efficiency and rapidly being established from Tables I, II and III as being greater than 75% efficiency and in times of not more than a few hours, preferably less than one hour) in water and thus avoiding solvent recovery and loss problems. The catalysts can be used in some alcoholic mediums as well as in some aqueous mediums. These catalysts are useful in catalytic asymmetric hydrogenation of some olefinic compounds. The new phosphine compounds are made from novel phosphine oxides.

8 Claims, No Drawings

OPTICALLY ACTIVE PHOSPHINE COMPOUNDS

BACKGROUND OF THE INVENTION

This invention relates to new optically active phosphine compounds which are useful in making optically active catalysts which are useful in catalytic asymmetric hydrogenation of some olefins. The new phosphine compounds are made from novel phosphine oxides.

Homogeneous catalysts, i.e. those catalysts that are soluble in the reaction mass, have been found to be particularly useful in processes wherein an asymmetric result is obtained. For instance, it has been found that when some olefins, which are capable of forming racemic mixtures are hydrogenated in the presence of some optically active homogeneous catalysts, one or the other of the possible desired optical enantiomorphs is obtained in a major amount with the other optical enantiomorph being obtained in minor amounts. Furthermore, it has been found that certain such olefinic substrates, for instance, precursors of $\alpha$-amino acids, are particularly amenable to hydrogenation with homogeneous optically active catalysts. Such procedures are set forth more particularly in Canadian Pat. No. 937,573. Such catalytic asymmetric hydrogenation processes have resulted in the production of large amounts of the desired optical enantiomorph.

Typical prior art catalyst are described in U.S. Pat. Nos. 3,849,480; 4,008,280; 4,119,652; and 4,166,824. Some of these catalysts are also described in the Journal of the American Chemical Society 99, (1977), page 5946, by Vineyard, Knowles, Sabacky, Bachman and Weinkauff in an article entitled "Asymmetric Hydrogenation: Rhodium Chiral Bisphosphine Catalyst."

Unlike the catalysts of the prior art, the catalysts of the invention can be used in water media and still give high efficiency and perform rapidly for asymmetric hydrogenation. The terms "high efficiency" and "perform rapidly" are defined throughout this patent application based on Tables I; II and III as being greater than 75% efficiency and in times of not more than a few hours, preferably less than one hour.

SUMMARY

The invention is a new family of phosphine compounds which can be used to make optically active metal coordination complex catalysts which combine high efficiency with a capability of performing rapidly in water and thus avoiding solvent recovery and loss problems. The catalysts can be used in some alcoholic mediums as well as some aqueous mediums. These catalysts are useful in catalytic asymmetric hydrogenation of some olefinic compounds. The new phosphine compounds are made from novel phosphine oxides.

The new phosphine compounds are made from novel optically active phosphine oxides of the formula

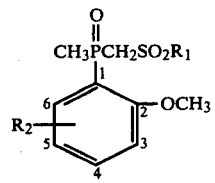

wherein $R_1$ is methyl, N,N-dimethylamino or morpholino and can be a wide range of alkyl, aryl or dialkylamino radicals in which the alkyl and aryl groups may be either hydrocarbon or substituted with organic or inorganic radicals. The range of $R_1$ is limited, however, by the requirements that it does not interfere with the necessary solubility properties or with the catalytic process. $R_2$ is hydrogen and an alkyl or aryl radical (again either hydrocarbon or substituted with organic or inorganic radicals) or inorganic radicals. $R_2$ must be in the 3,4 or 5 position. Some inorganic radicals that would be expected to be compatable are Cl, Br, I, F and sulfone. The range of $R_2$ is limited by the requirements that it does not interfere with the necessary solubility properties or with the catalytic process.

The new phosphine compounds made from the phosphine oxides will then be of the formula

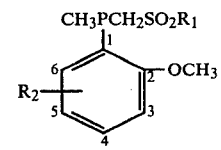

wherein $R_1$ and $R_2$ are as defined hereinabove.

The optically active metal coordination complex catalyst precursor comprises rhodium metal and two moles per mole of metal of phosphine ligand. The ligands are those described in the previous paragraph.

The invention will be more clearly understood from the following detailed description of specific examples thereof.

The new chiral ligands illustrative of this invention have the following structures:

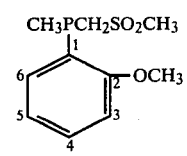 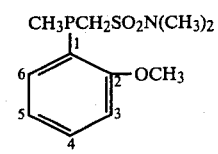

IV  VI

They were made from the corresponding new optically active phosphine oxides:

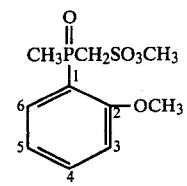 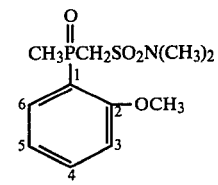

III  V

The catalyst as shown in Table I may be used by combining two ligands and one rhodium or a solid complex may be used of the following structure where L is the phosphine ligand and COD is 1,5-cyclooctadiene.

$[L_2RhCOD]^+ClO_4^-$

The substrate (i.e. z-$\alpha$-acetamidocinnamic acid) can be hydrogenated as the free acid (A) or the water soluble sodium salt (B). The solvent can be varied from pure water to 50% methanol to 88% isopropyl alcohol. It should be emphasized that the previously described catalyst precursors will not hydrogenate well, if at all, in water solvent even though the complex added is ionic.

TABLE I
REDUCTION OF Z—α-ACETAMIDO CINNAMIC ACID WITH LIGAND IV RHODIUM CATALYST[1]

| Cat. | Temp. °C. | psig | Solvent | Time hrs. | % ee | Remarks |
|---|---|---|---|---|---|---|
| solid | 50 | 50 | 88% IPA A | 0.2 | 79.7 | |
| solid | 50 | 50 | H$_2$O A | 0.4 | (73) | 95% done |
| in situ | 50 | 50 | 4% MeOH B | 0.3 | 83 | |
| solid | 50 | 50 | H$_2$O B | 0.4 | 82.5 | |
| in situ | 0 | 50 | 50% MeOH B | 3.0 | 91.5 | |
| solid | 0 | 50 | 4% MeOH B | 2.0 | 92.5 | |

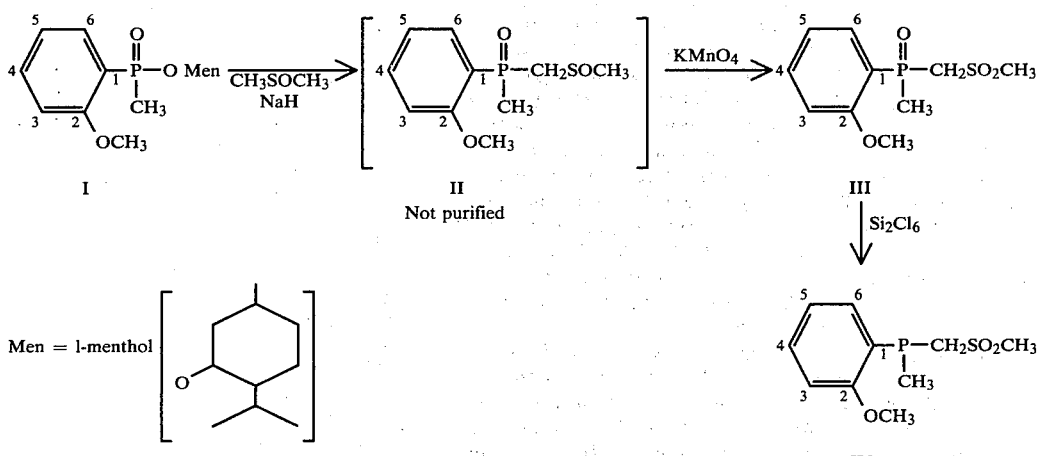

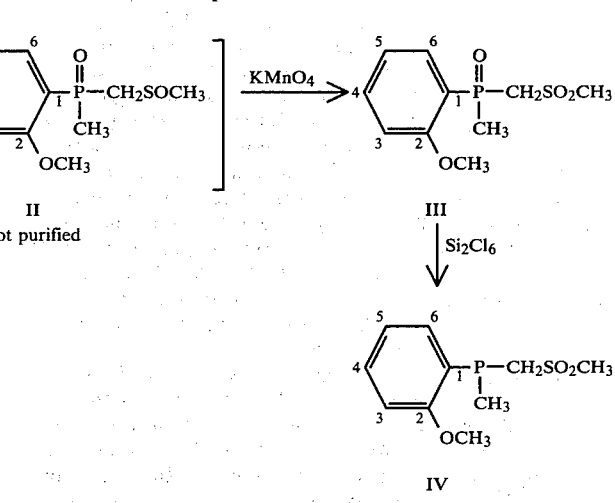

[1]Hydrogenations were run with 1000/1 molar ratio of substrate to metal.

TABLE II
REDUCTION OF Z—α-ACETAMIDO CINNAMIC ACID WITH LIGAND VI RHODIUM CATALYST[2]

| Cat. | Temp. °C. | psig | Solvent | Time hrs. | % ee |
|---|---|---|---|---|---|
| solid | 50 | 50 | 50% MeOH B | 0.2 | 84 |
| in situ | 50 | 50 | 88% IPA A | 0.1 | 78 |
| in situ | 50 | 50 | 3% MeOH B | .4 | 86 |

[2]Hydrogenations were run with 1000/1 molar ratio of substrate to catalyst.

TABLE III
REDUCTION OF Z—α-ACETAMIDO CINNAMIC ACID WITH MORPHOLINO LIGAND[3] RHODIUM CATALYST[4]

| Cat. | Temp. °C. | psig. | Solvent | Time hrs. | % ee |
|---|---|---|---|---|---|
| in situ | 0 | 50 | MeOH(B) | ~2 | 90 |

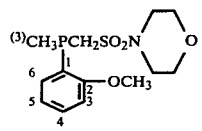

Morpholino Ligand
S—(O—Methoxyphenyl)methyl(morpholino-sulfonylmethyl)phosphine
[4]Hydrogenations were run with 1000/1 molar ratio of substrate to metal.

EXAMPLE 1

Hydrogenation Procedure: A 65 ml pressure vessel was charged with 1.000 g (4.9 m moles) Z-α-acetamidocinnamic acid, 25 ml of solvent and then purged to remove residual air. Then it is set at the desired pressure of hydrogen and temperature. The catalyst equivalent to 0.005 m mole of rhodium is made in 95% methanol by adding two equivalents of ligand to one equivalent of rhodium as (Rh(COD)Cl)$_2$ or Rh(COD)AcAc where COD=1,5-cyclooctediene and AcAc=CH$_3$COCOCH$_3$. The catalyst is then added through a septum to the batch and the hydrogenation run until gas uptake ceases. The percent ee is measured directly by diluting to volume and comparing the rotation with a standard. When the solid complex is used as catalyst, it is added directly before purging.

The new compounds are made as follows:

EXAMPLE 2

(2 Methoxyphenyl) methyl[(methylsulfonyl)methyl] phosphine oxide III

In a dry 500 ml 3-neck round-bottom flask under nitrogen, place 9.7 g (231.5 m mole) of NaH as a 57% oil dispersion and wash several times with hexane to remove the oil. Then add 200 ml of dimethyl sulfoxide (DMSO) (stored over molecular sieves) and heat with stirring at 70°–75° C. until evolution of hydrogen ceases (ca. 45 min.). Let the solution warm to room temperature and then add the menthol ester (I) (25 g, 77.2 m moles) as a solid all at once and heat to 50° C. for 4 hours and let stir at room temperature overnight.

Dilute the reaction mixture with about two volumes of water and extract several times with chloroform.

Combine the organic extracts and concentrate under reduced pressure (~20 mm Hg). Then remove the generated menthol by distilling under high vacuum while heating with a water bath (~90° C.).

The residue, a tan oil, having a mass spectra and nmr consistent with structure II was used without purification.

This material was oxidized to the sulfone by dissolving the oil in acetic acid (300 ml) and treating with 3% aqueous KMnO$_4$ (1000 ml). The oxidation is only slightly exothermic and appears to be finished in minutes; therefore, the solution of the sulfoxide in AcOH and KMnO$_4$ solution are combined quickly and allowed a reaction time of about 30 minutes. The resulting dark brown mixture is treated with solid sodium metabisulfite until the MnO$_2$ dissolves and this solution is extracted with CHCl₃ (5×250 ml). The combined extracts are concentrated under reduced pressure to give a white solid which can be crystallized from toluene or water to give white crystals.

Yield 3.6 g (19%) mp 172°-4° C. Mass spectra parent ion 262. Further purification gives a material m.p. 175°-6° C. $[\alpha]_D^{20} + 70.2$ (C=0.8 in MeOH).

EXAMPLE 3

(2-Methoxyphenyl)methyl[methyl sulfonyl)methyl] phosphine IV

Prepare, under N₂ in a dry 3-neck 250 ml round-bottom flask, a solution of (III) (0.87 g, 3.32 m mole) in acetonitrile (75 ml, dried over molecular sieves) and heat at reflux. Add via. syringe Si₂Cl₆ (1.7 ml, 3 eq) and after another 15 minutes a final equal portion of Si₂Cl₆ (1.7 ml, 3 eq). After this last portion, let the reaction continue at reflux for 1 hour and then let it cool to room temperature.

Under nitrogen, add the reaction mixture portionwise to an ice-cold solution of 25% aqueous NaOH (60 ml, purged with nitrogen) and let warm to room temperature. Extract this solution several times with CHCl₃* solid concentrate at reduced pressure to give a white solid which can be crystallized from ethanol to give a white crystalline solid.
*Extraction of a sodium hydroxide solution with chloroform could be dangerous and the use of CH₂Cl₂ is recommended rather than chloroform.

The nmr was consistent with structure IV. $[\alpha]_D^{20} + 131$ (C=0.4 in ab EtOH).

EXAMPLE 4

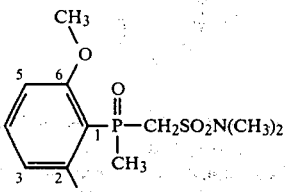

[(N,N-dimethylaminosulfonyl)methyl](2-methoxy)-methyl phosphine oxide

In a dry 500 ml 3-neck round-bottom flask under N₂, prepare a solution of CH₃SO₂N(CH₃)₂ (10.43 g, 0.0848 mole) and tetrahydrofuran (THF) (100 ml, distilled from Na and benzophenone) and cool to about 10° C. To this stirred solution at 10° C., add n-butyl lithium (50.9 ml, 0.0815 mole, 1.6 M in hexane) dropwise so the temperature remains below 15°-20° C. (a ppt of the lithium salt forms). This solution is let stir at 15° C. for about 15 minutes.

A solution of the menthol ester (I) (11.0 g, 0.034 mole) in dry THF (50 ml) is added quickly at 15° C. and then the reaction mixture is warmed to room temperature and let stir overnight. After this period, the reactor mixture was clear and light yellow. Analysis by thin layer chromatography (TLC) on silica gel with ethyl acetate showed that essentially all the starting material was gone.

The reaction mixture was quenched with excess acetic acid (20 ml) and concentrated under reduced pressure. The residue was dissolved in CHCl₃ (250 ml) and this was washed with a small amount of water (100 ml). The aqueous wash was extracted with CHCl₃ (2×250 ml) and the organic phases were concentrated under reduced pressure. The residue, a yellow-tan oil, was purified on dry column chromatography with silica gel and ethyl acetate to give a light tan solid which was dissolved in hot toluene and filtered to give a white solid (9.1 g, 76%) which crystallizes from toluene. The mass spectra and nmr are consistent with structure V. mp=143°-4° C. $[\alpha]_D^{20} + 59.8$ (c=2.6 in MeOH).

EXAMPLE 5

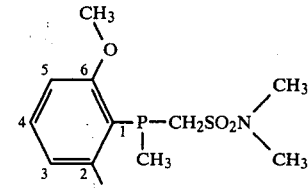

[(N,N-dimethylsulfonyl)methyl](2-methoxyphenyl)methylphosphine

Prepare, under N₂ in a dry 250 ml 3-neck round-bottom flask, a solution of the phosphine oxide (V) (1.0 g, 3.4 m mole) in acetonitrile (80 ml, dried over molecular sieves) and heat to reflux. To this refluxing solution add 2.0 ml (3 eq) of Si₂Cl₆ and let the reaction proceed for 15 minutes. Then add an additional 1.0 ml (1.5 eq) of Si₂Cl₆ and continue to heat at reflux for 30 minutes. Cool the reaction mixture to 0° C. and add it in portions under N₂ to an ice-cold mixture of benzene (300 ml, purged with N₂) and 25% aqueous NaOH (50 ml, purged with N₂). The layers were separated and the benzene layer was washed with water (2×30 ml) (again all under N₂) and the original aqueous NaOH layer was washed with CHCl₃*. The organic extracts were combined and concentrated at reduced pressure to give an airsensitive yellow oil (~1.0 g, near quantitative yield).
*Extraction of a sodium hydroxide solution with chloroform could be dangerous and the use of CH₂Cl₂ is recommended rather than chloroform.

This oily material can be purified by converting to a rhodium complex and crystallizing out of 88% IPA. The rhodium complex which is air sensitive has the following structure:

L₂ Rh AcAc, where L=ligand VI and AcAc=CH₃COCOCH₃.

This material was used in the catalytic hydrogenations.

EXAMPLE 6

(S)-(O-Methoxyphenyl)methyl(morpholinosulfonylmethyl)phosphine

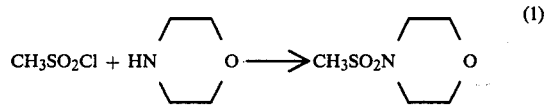

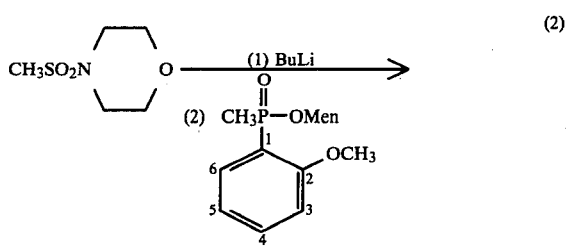

-continued

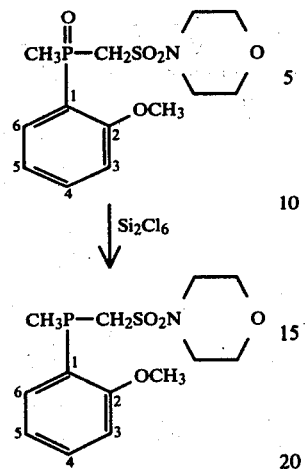

To a solution of morpholino methyl sulfonamide (14.0 g, 84.9 m mole) in 100 ml dry tetrahydrofuran (THF) at 15° C. was added n-butyl lithium (50.9 ml of 1.6 M solution in hexane, 81.5 m moles). Then (S)-p-menthyl-O-methoxyphenyl methylphosphinate (11.0 g, 34.0 m moles) in 50 ml dry THF was added at 15° C. and the mass was held at 20°-25° C. for 16 hours giving a clear yellow solution. This intermediate product was purified on a dry silica column by elution with ethyl acetate.

Nuclear magnetic resonance (NMR) in CDCl$_3$ S 1.96(d,3H,J=14 Hz), 3.20-3.90(m,8H), 3.55(d,2H,J=14.H$_2$), 3.92(S,3H) and 6.74-8.11(m,4H). This solid intermediate product (2.26 g, 6.8 m moles) was dissolved in 150 ml of dry acetonitrile and 6 ml of Si$_2$Cl$_6$ were slowly added at 70° C. The mixture was then held for 30 minutes, cooled and added to 100 ml of 25% NaOH at 0°-5° C. The layers were separated and the aqueous phase extracted with CH$_2$Cl$_2$. After removal of the solvent 1.9 g of clear yellow oil was obtained. It was crystallized from ethanol to give a product, m.p. 76°-77° C., [α]$_D^{20}$+123.8° C. (C=0.8 in CHCl$_3$). Mass spectrometer (MS) and nuclear magnetic resonance (nmr) analysis were consistent. Further crystallization did not improve the rotation.

Although the invention has been described in terms of specified embodiments which are set forth in considerable detail, it should be understood that this is by way of illustration only and that this invention is not necessarily limited thereto, since alternative embodiments and operationg techniques will become apparent to those skilled in the art in view of the disclosure.

What is claimed is:

1. An optically active phosphine oxide of the formula

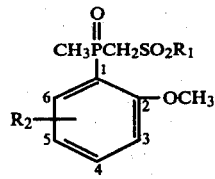

wherein R$_1$ is an alkyl, aryl or dialkylamino radical; R$_2$ is hydrogen or an alkyl, aryl, Cl, Br, I, F or sulfone radical; any of said alkyl and aryl radicals may be substituted with Cl, Br, I, F and/or sulfone radicals; R$_2$ is in the 3, 4 or 5 position; and R$_1$ and R$_2$ do not interfere with the necessary solubility properties or with the catalytic process.

2. A phosphine oxide of claim 1 wherein R$_1$ is methyl and R$_2$ is hydrogen.

3. A phosphine oxide of claim 1 wherein R$_1$ is dimethylamino and R$_2$ is hydrogen.

4. A phosphine oxide of claim 1 wherein R$_1$ is morpholino and R$_2$ is hydrogen.

5. An optically active phosphine of the formula

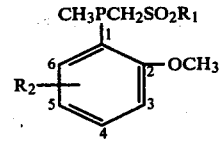

wherein R$_1$ is an alkyl, aryl or dialkylamino radical; R$_2$ is hydrogen or an alkyl, aryl, Cl, Br, I, F or sulfone radical; any of said alkyl and aryl radicals may be substituted with Cl, Br, I, F and/or sulfone radicals; R$_2$ is in the 3, 4 or 5 position; and R$_1$ and R$_2$ do not interfere with the necessary solubility properties or the catalytic process.

6. A phosphine of claim 5 wherein R$_1$ is methyl and R$_2$ is hydrogen.

7. A phosphine of claim 5 wherein R$_1$ is dimethylamino and R$_2$ is hydrogen.

8. A phosphine of claim 5 wherein R$_1$ is morpholino and R$_2$ is hydrogen.

* * * * *